United States Patent [19]

Koocher et al.

[11] Patent Number: 4,816,414
[45] Date of Patent: Mar. 28, 1989

[54] METHODS AND APPARATUS FOR DETECTING AN ANALYTE OF INTEREST CAPABLE OF BEING CONVERTED INTO A CARBONYL-CONTAINING COMPOSITION

[75] Inventors: Martin Koocher, Lexington; Nathan O. Siemers, Allston, both of Mass.

[73] Assignee: Crystal Diagnostics, Inc., Woburn, Mass.

[21] Appl. No.: 105,138

[22] Filed: Oct. 2, 1987

[51] Int. Cl.$^4$ .......................... G01N 1/10; G01N 21/00
[52] U.S. Cl. ........................................ 436/85; 436/128; 436/86; 422/58
[58] Field of Search ...................... 422/58, 84, 85, 86; 436/170, 124–126, 128, 142, 902

[56] References Cited

U.S. PATENT DOCUMENTS

| 3,399,973 | 9/1968 | Grosskopf | 422/60 |
| 3,437,449 | 4/1969 | Luckey | 422/85 |
| 3,711,251 | 1/1973 | Goodson et al. | 436/130 |
| 3,997,416 | 12/1976 | Confer | 436/126 |
| 4,144,306 | 3/1979 | Figueras | 422/56 |
| 4,380,587 | 4/1983 | Koocher | 436/128 |
| 4,489,164 | 12/1984 | McConnaughey et al. | 436/130 |
| 4,740,475 | 4/1988 | Paul | 436/165 |
| 4,758,521 | 7/1988 | Lushbaugh et al. | 436/128 |

FOREIGN PATENT DOCUMENTS

658475  4/1979  U.S.S.R. .

Primary Examiner—Barry S. Richman
Assistant Examiner—Lyle Alfandary-Alexander
Attorney, Agent, or Firm—David Prashker

[57] ABSTRACT

The present invention provides unique methods and apparatus for the detection of an analyte of interest in a fluid sample by selective oxidation of the analyte into a carbonyl-containing compound followed by the controlled formation and growth of optically visible crystals as a qualitative and quantitative measure of the analyte. Epoxides, alcohols, olefins, arylalkanes and alkyl halides are among the many different classes or chemical entities which can be selectively detected in the concomittant presence or absence of other substances within the test sample.

38 Claims, 5 Drawing Sheets

METHODS AND APPARATUS FOR DETECTING AN ANALYTE OF INTEREST CAPABLE OF BEING CONVERTED INTO A CARBONYL-CONTAINING COMPOSITION

FIELD OF THE INVENTION

The present invention is concerned with methodologies and apparatus for the qualitative and quantitative detection of an analyte of interest and is directed to detection of analytes which can be selectively converted into carbonyl-containing compositions followed by selective formation and growth of optically visible crystals.

BACKGROUND OF THE INVENTION

In recent years there has been growing concern and interest over the presence and biological effects of chemical contaminants which are either in water or airborne in the workplace or the home environment. Governmental agencies, employers, and the community at large now recognize the dangers of breathing or ingesting chemical contaminants released into the air and water at home and/or in industry. The dangers and concerns have reached such proportions that governmental agencies such as the FDA, OSHA, and NIOSH now publish lists of chemically hazardous and/or toxic substances and identify the maximum exposure limit considered safe and non-hazardous for each; as well as provide specific methods for the detection and quantitative measurement of these toxic and/or hazardous chemical compositions.

Representative of these dangers and public concerns is the problem regarding ethylene oxide contamination. Ethylene oxide sterilization is used extensively in hospitals and clinical institutions and by many drug and device manufacturers. A recent survey identified 250 services representing 10 billion units per year sterilized by use of ethylene oxide. The utility of this compound for sterilization purposes resides in its inherent toxicity which also makes it imperative that it be handled with extreme care; and that sensible precautions be taken to avoid hazardous or accidental release. OSHA has placed severe limits on the exposure in (parts-per-million) considered safe for persons working with ethylene oxide. Employees working with this toxic compound are typically exposed to traces of ethylene oxide after opening sterilizer doors and upon the degassing of products and packages after sterilization. The ideal method of assessing the risk and the degree of worker exposure is personal monitoring [Romano and Renner, *AM. IND. HYG. ASSOC. J.* 40;742(1979)].

A variety of other toxic substances have also been identified. The list comprises not only epoxides such as ethylene oxide; but also includes primary and secondary alcohols, glycols, unsaturated olefins of aliphatic and aromatic structure, and the like. A variety of different methods and apparatus have been developed to detect the presence of such chemical compositions and to quantitate their concentration. Of these, the published NIOSH methods remain the standard for this purpose. These methodologies generally, however, are technically difficult, require sophisticated analytical instrumentation, and are cumbersome and time consuming. Some alternatives for monitoring exposure to these chemicals have been developed. These include personal monitoring apparatus involving a variety of different chemical reactions. For example, U.S. Pat. No. 3,714,562 discloses the use of a metallic film to absorb a selected chemical vapor, the presence of the vapor being measured by a change in the resistance of the film. Similar resistance-type systems are described by U.S. Pat. Nos. 3,703,696 and 3,950,980. Another personal detection monitoring system is disclosed by Palmes and Gunnison [*American Industrial Hygiene Association Journal* 34;78081(1973)]. This described device measures a chemical contaminant as a function of vapor concentration. The process required to identify and/or quantify the vapor exposure within the device requires the sophistication and expense of a well equipped analytical laboratory. More recently, U.S. Pat. No. 4,380,587 describes a film badge for determining carbonyl compounds with a specific direct application to the detection of formaldehyde. This innovation employs the formation and growth of an optically measureable film of crystals to determine the concentration of the carbonyl compound in the test sample. The use of this crystal growing methodology was also employed within the invention of copending application Ser. No. 862,072 filed May 12, 1986, and about to issue as U.S. Pat. No. 4,727,024 on Feb. 23, 1988. The invention described within this patent application employs a prepared conjugate reactant having specific binding properties for an analyte of interest capable of releasing a carbonyl-containing moiety which is subsequently detected by the formation and growth of optically visible crystals.

Despite these recent developments and innovations, there remains a continuing need for methods and apparatus which can detect a variety of different chemical compositions in the air and water. Much of the difficulty in creating a non-instrument, personal monitoring apparatus lies in the fact that non-hazardous and/or toxic substances vary greatly in chemical structure and reactivity; that more than one type of chemical composition is often present in the air or water within the workplace or at home; that the means for detecting each type of hazardous and/or toxic chemical composition is different and frequently unique to that type or class of chemical compound; and that the selectivity and reproducibility of non-instrument methods and apparatus is typically insufficient to detect very low levels of chemical substances and/or to provide accurate and reliable quantitative results. Clearly, therefore, any innovation which improves the sensitivity, reliability, and speed of a non-instrument method and apparatus able to detect a variety of chemically different substances in the ambient environment would be deemed a major advance and long desired achievement in this art.

SUMMARY OF THE INVENTION

The present invention provides a rapid method for detecting the presence of an analyte of interest in a fluid sample, this method comprising the steps of: reacting the fluid sample with an oxidizing agent selectively reactive with the analyte of interest to yield at least one oxidized product having at least one carbonyl group available for reaction; combining the oxidized product having the carbonyl group with a derivatizing agent to yield a reaction product formed as a plurality of nucleating sites in-situ, these nucleating sites being immobilized on the surface of a solid substrate; treating the nucleating sites with a metastable supersaturated solution such that a plurality of optically detectable crystals are formed; and optically detecting the formed crystals as a measure of the analyte of interest in the fluid sample.

Another aspect of the present invention provides a rapid method for selectively detecting an analyte of interest in a mixed fluid sample in the presence of at least one other substance, this method comprising the steps of: combining the fluid sample with a cleansing agent which reacts selectively with the other substance and is substantially unreactive with the analyte of interest to yield a cleansed sample free of the other substance; then reacting the cleansed sample with an oxidizing agent selectively reactive with the analyte of interest to yield at least one oxidized product having at least one carbonyl group available for reaction; combining the oxidized product with a derivatizing agent to yield a reaction product formed as a plurality of nucleating sites in-situ, these nucleating sites being immobilized on the surface of a solid substrate; treating the nucleating sites with a metastable, supersaturated solution such that a plurality of optically detectable crystals are formed; and optically detecting the presence of the formed crystals as a measure of the analyte of interest in the sample.

The apparatus provided by the present invention provides specific means to perform these methods in a dry, solid format as opposed to traditional wet reaction chemistries and formats. The apparatus provides each cleansing agent, oxidizing agent, and derivatizing agent in a dry solid state with the desired selectivity to discriminate among mixtures of chemical contaminants of different formulae and structures and to quantitatively measure the analyte of interest present in such mixtures accurately and reproducibly.

BRIEF DESCRIPTION OF THE DRAWING

The present invention may be more fully and easily understood when taken in conjunction with the accompanying drawing, in which.

DETAILED DESCRIPTION OF THE PREFERRED EMBODIMENTS

The present invention is a generally useful assay methodology for the detection of a non-carbonyl containing analyte of interest in a gaseous or liquid sample in a qualitative and/or quantitative manner. The apparatus of the present invention is a non-instrument device, a film badge, which provides the requisite reactants in the proper sequence of manipulative steps for reactive formation and growth of optically detectable crystals on a solid substrate. The performance of the unique methods for detection utilizing these innovations and improvements provides accurate, reproducible, qualitative and quantitative assays for the detection of a wide variety of different chemically hazardous/toxic substances.

The present invention offers a selective capability to detect specific chemical entities not only among the different chemical classes of compounds [epoxides, alcohols, olefins, and the like]but also between individual members of a single class [ such as between primary and secondary alcohols]. This selective detection capability is maintained within a variety of different test environments and samples so long as the analyte of interest does not initially contain a carbonyl group as part of its chemical formula or structure. For example, the fluid test sample can comprise a mixture of different classes of chemical compounds such as a mixture of ethylene oxide (an epoxide) and ethanol (an alcohol); alternatively, the fluid test sample may contain a mixture of two members of the same chemical class such as ethanol (a primary alcohol) and isopropyl alcohol (a secondary alcohol); a third possibility is the presence of one or more other substances such as aldehydes and/or ketones which are present within the sample with the analyte of interest thereby providing a mixture of one or more chemical entities; lastly, and most simply, the sample may comprise the non-carbonyl analyte of interest alone in a gaseous or liquid carrier. Any and all of these test circumstances and environments may provide the fluid test sample for analysis using the present methodology and apparatus.

In view of the diversity and variety of chemical entities, alone or in mixture, permitted to be present as part of the initial test sample for analysis, it is clear that a major part of the uniqueness and advance provided by the present invention resides in its ability to selectively detect and measure a single non-carbonyl analyte of interest despite the presence of other incidental chemical substances and analogues which may be very similar chemically and/or structurally to the true analyte of interest within the sample.

The selectivity and accuracy of the methodology and apparatus comprising the subject matter as a whole of the present invention is provided and controlled by two, and optionally three, independent factors which can be used individually or in any combination: Initially, selectivity may be controlled by the choice of oxidizing agent to be combined with the test sample; this oxidizing agent selectively reacts with the analyte of interest to yield at least one oxidized product having at least one carbonyl group available for reaction. The particular oxidizing agent employed must thus be chosen with a view to the entirety of other chemical entities which may be present within the test sample such that only the analyte of interest is oxidized into a carbonyl-containing composition; all other chemical entities present as part of the initial test sample must either remain unreactive to the chosen oxidizing agent or become oxidized by the oxidizing agent to yield the corresponding carboxylic acid (COOH) reaction product.

The second selective factor and point of control within the assay methodology is provided by the composition of the metastable supersaturated solution employed to form and grow optically detectable crystals. The specificity is provided by the crystal growing event in that unless the analyte of interest has been converted by a series of chemical reactions into nucleating sites, the chemical composition of which is identical with the formula and structure of the composition comprising the metastable supersaturated solution, no optically detectable crystals will be formed. Closely analogous compositions comprising chemical entities other than the analyte of interest will not, therefore, initiate crystal growth.

The third, optional, basis for selectivity and control lies in the use of specific cleansing agents which react with other substances which may be present in the initial test sample. These cleansing agents are selective, chemically active compositions which act to remove the undesirable other substances which could potentially interfere with the accuracy, precision and/or sensitivity of the assay method by reacting with them to yield non-reactive, non-carbonyl containing products. The use of cleansing agents precedes the combination of the sample with the selective oxidizing agent within the stated series of reactive steps.

In order to properly appreciate and fully understand each of the methods provided by the present invention, a detailed review of each manipulative step and a complete description of each individual reactant employed is provided. In this manner, the distinguishing features of the individual reactions and the major advantages of the present methodology and apparatus as a whole will become apparent.

The Analyte of Interest

The method and apparatus of the present invention may be employed to detect and to measure qualitatively and quantitatively a wide variety of non-carbonyl chemical compositions as the analyte of interest. The first requirement is that the analyte of interest not initially be a composition containing one or more carbonyl groups available for reaction. Accordingly, the chosen analyte includes but is not limited to the classes of: epoxides; alcohols; olefins; aliphatic and aromatic compositions such as arylalkanes, and the like. The second limitation for detection purposes is that the analyte of interest be convertible into a composition having a reactive carbonyl group as part of its formula and structure.

The Cleansing Agent

The preferred methodology utilizes a selective cleansing agent for combination with the initial test sample as the first manipulative step. The cleansing agent is a reagent which reacts selectively with such interfering substances as may be present as part of the initial test sample; and concomittantly is a reagent substantially unreactive with the analyte of interest believed to be present in the sample. The cleansing agent selectively combines with only these interfering substances to yield a cleansed sample comprising only non-carbonyl chemical compositions.

The selectivity of the cleansing agent is directed towards different individual classes of interfering substances. Representative of the various chemical classes are those listed in Table I.

TABLE I

| Interfering Substances | Preferred Cleansing Agent |
|---|---|
| organic and inorganic acids (H+) | sodium carbonate |
| ammonia and amines | citric acid |
| cyanides | silver nitrate |
| aldehydes and ketones | nicotinic acid hydrazide |

The preferred cleansing agent for removing aldehydes and ketones in the initial test sample is nicotinic acid hydrazide. Other reagents useful as cleansing agents in the present methodology include: semicarbazide; 2,4-dinitrophenylhydrazine; para-nitrophenyl hydrazine; phenyl hydrazine; and thioscemicarbazide. In addition, should any of these not be deemed convenient or desirable by the user, additional choices for the selective cleansing agent include all the specific compositions identified as derivatizing agents as these will be described and reviewed hereinafter. It will be recognized and appreciated, therefore, that the selectivity and function of these cleansing agents is to remove undesirable, potentially interfering, aldehydes and/or ketones which may be present in the initial test sample—thereby providing the means for selective control, accuracy, precision, and sensitivity for the methodology as a whole.

The preferred cleansing agent for removing potentially interfering organic and inorganic acids is sodium carbonate. Other reagents useful as cleansing agents include: alkali and alkaline earth hydroxides, carbonates, and bicarbonates.

The preferred cleansing agent for removing potentially interfering ammonia and amines is citric acid. Other useful cleansing agents include organic acids generally such as tartaric acid, succinic acid, oxalic acid, and maleic acid.

The preferred cleansing agent for removing potentially interfering cyanides is silver nitrate. Other useful cleansing agents for this chemical class include other salts of silver and salts of nickel, copper, and iron.

Within the preferred apparatus of the present invention, the cleansing agent is employed as a dry, solid reactant absorbed onto a porous support pad. The cleansing agent is thus employed in a "dry" state or format and is held in physical position by a reagent pad, preferably via a material such as polyethylene formed as a porous matrix (commercially available from Porex Technologies). The porous polyethylene pad is preferably pretreated by soaking the pad material in anhydrous methyl alcohol for approximately one hour's duration to remove any impurities which might be present. The freshly washed pads are then filtered from the methyl alcohol using a narrow-stem glass funnel and allowed to drain free of liquid. After about 15 minutes, drained pads are preferably placed in a clean room where they are allowed to air-dry. Subsequently, presuming the cleansing agent to be nicotinic acid hydrazide (hereinafter "NAH"), a solution of 3% NAH/1% citric acid in methanol is prepared by combining 7.5 grams of NAH and 2.5 grams of citric acid monohydrate with 250 milliliters of reagent-grade methanol. This mixture is stirred vigorously or sonicated until all of the NAH and citric acid have dissolved in the methanol. The quantity of prepared NAH/citric acid solution—the cleansing agent—can be varied in accordance with the number of porous pads to be prepared. Sufficient liquid mixture should be prepared to completely submerge all the porous pads concurrently. Once the 3% NAH/1% citric acid/methanol solution has been prepared, the pads are submerged in the liquid and stirred vigorously for approximately one hour to ensure that all the porous pads have become imbibed with the cleansing agent. Subsequently, the pads are filtered from the cleansing agent solution using a narrow-stem glass funnel and allowed to drain. The prepared pads are then preferably allowed to air dry for 1-2 hours before vacuum drying at ambient temperature for 20 hours' duration. After vacuum drying, the prepared cleansing agent pads are placed in a sealed container containing an abundance of a dessicant such as 50/50 silica charcoal. Once sealed with the dessicant material the prepared dry pads may be stored at room temperature indefinitely until required for use.

In some instances porous pads other than those made from polyethylene can be used. These would include pads made from polypropylene, glass fiber, or "Kynar." In some instances solvents other than methanol can be used to dissolve the cleansing reagent. Alternatively the addition of wetting agents and/or surfactants may be necessary or beneficial as well.

The Selective Oxidizing Agent

After the chemical entities comprising the potential interfering substances in the initial test sample have been removed by the cleansing agent, the sample is then reacted with an oxidizing agent which is selectively reactive with the analyte of interest to yield at least one oxidized product having at least one carbonyl group available for reaction. The purpose and function, therefore, of the oxidizing agent is to selectively react with the analyte of interest in the presence of other chemical entities; and to oxidize the analyte of interest into a reaction product which is chemically either an aldehyde or ketone. It will be appreciated, therefore, that the selectivity and control provided by the oxidizing agent employed lies in choosing a reagent which will react selectively with the analyte of interest alone and concomitantly control the degree of oxidation such that the production of the corresponding carboxylic acid is avoided.

The present state of technical knowledge regarding oxidation reactions and their control for different kinds and classes of chemical entities is extensive and well described in the literature. Representative and descriptive of the present state of knowledge and the variety of different enzymatic and non-enzymatic oxidizing agents are: J. David Rawn, *Biochemistry*, Harper & Row, New York, 1983, and Gerry March, *Advanced Organic Chemistry* (Reactions, Mechanisms, And Structure), third edition, John Wiley and Sons, 1985, the texts and cited references of which are expressly incorporated by reference herein.

While the scientific literature provides an extensive listing of oxidizing agents in general and for different classes of chemical compounds, the present invention chooses from among all these possible choices utilizing two criteria: First, that the chosen oxidizing agent be as selective as possible such that solely the analyte of interest be oxidized to yield a product having at least one carbonyl group available for further reaction. Second, that the degree of oxidation be limited and controlled to insure that at least one aldehyde or ketone reaction product is yielded from the analyte of interest and that further oxidation of the analyte into the corresponding carboxylic acid is suppressed. Both criteria should be met in order for the individual oxidizing agent to qualify for use within the present invention. Accordingly, a non-exhaustive listing of preferred oxidizing agents is provided by Table II for specific members of different chemical classes including epoxides, alcohols, alkenes, arylalkanes and primary alkylhalides. It will be clearly understood and recognized that the specified individual chemical classes identified by Table II are merely representative of the diversity and wide variety of other chemical entities and classes which can be detected using the methodology of the present invention; and that the present methodology is not limited nor restricted to these listed chemical classes nor to the individual members identified within any of these chemical classes.

TABLE II

| Analytes | Preferred Oxidizing Agent |
| --- | --- |
| Epoxides: | |
| ethylene oxide | Periodic acid |
| epichlorohydrin | Periodic acid |
| Alcohols: | |
| 2-butoxylethanol | 3-carboxypyridinium dichromate |
| butyl alcohol | 3-carboxypyridinium dichromate |
| cyclohexanol | Manganese dioxide |
| isopropyl alcohol | Manganese dioxide |
| methyl cellosolve | 3-carboxypyridinium dichromate |
| Olefins: | |
| styrene | Potassium permanganate |
| ethylene | Palladium chloride and cupric chloride |
| Aryl alkanes: | |
| p-xylene | Ceric ammonium nitrate |
| m-chlorotoluene | Ceric ammonium nitrate |
| Primary alkyl halides: | |
| allyl chloride | 4-dimethylaminopyridine-N—oxide |
| propyl chloride | 4-dimethylaminopyridine-N—oxide |

In addition, it should be appreciated that the selectivity of the oxidizing agent and the manner of its choosing is properly performed using two additional levels of perspective and evaluation. Initially, selectivity is evaluated with respect to the class of the analyte of interest to be detected; secondarily, the selectivity of the chosen oxidizing agent must be evaluated with respect to the nature and reactivity of the other chemical entities which might be present as part of the initial test sample. This dual evaluation criteria and requirement is unique to the present invention.

The initial requirement is met by recognizing that certain kinds of oxidizing agents are most preferred for certain classes of chemical compounds. For example, periodic acid and lead tetraacetate are selectively reactive with both epoxides and 1,2-diols; alcohols are selectively oxidized into aldehydes using manganese dioxide, 3-carboxy pyridinium dichromate, and ceric ammonium nitrate. Similarly, alkenes are converted into aldehydes and ketones using osmium tetroxide/sodium periodate, acid permanganate, and dichromate. Each of these oxidizing agents will selectively react with the members of the individual chemical class and the analyte of interest to yield a product having at least one carbonyl group.

The second level of selective evaluation for the oxidizing agent to be chosen refines and narrows the evaluation to avoid oxidizing other chemical entities suspected of being present in the initial test sample. Accordingly, therefore, oxidizing agents are chosen not only with respect to the chemical class or broad chemical structure but also with respect to individual characteristics which distinguish among members within a single chemical class. For example, among the oxidizing agents able to convert alcohols to aldehydes, individual oxidizing agents can be chosen which specifically oxidize a secondary hydroxyl group in the presence of a primary hydroxyl group; these include Cl₂-pyridine, (Bu₃Sn)₂O-Br₂, sodium bromate-ceric ammonium nitrate, and sodium hypochlorite. In comparison there is a small but identifiable group of selective oxidizing agents which oxidize primary hydroxyl groups in the presence of a secondary hydroxyl group. These include RuCl₂(PPh₃)₃ and Br₂-Ni(OBz)₂, respectively. Analogously, monosubstituted and 1,2-disubstituted olefins are selectively oxidized into aldehydes and ketones by palladium chloride and similar salts of noble metals; other olefins generally are non-reactive with these specific oxidizing agents.

To further demonstrate the exquisite sophistication and individual sensitivity of the oxidizing agent which can be chosen to distinguish among different chemical entities and an analyte of interest when these are present as a mixture, an illustrative series of selective Reaction Sequences, A-H, are provided. Reaction Sequence A demonstrates the selective oxidation of an epoxide in the presence of a primary alcohol; Reaction Sequence B demonstrates the selective oxidation of an 1,2-diol in the presence of a monohydroxy alcohol; Reaction Sequence C illustrates the selective oxidation of a secondary alcohol in the presence of a primary alcohol; Reaction Sequence D describes another selective oxidation of a secondary alcohol in the presence of a primary alcohol; Reaction Sequence E describes the selective oxidation of a primary alcohol in the presence of a secondary alcohol; Reaction Sequence F illustrates the selective oxidation of monosubstituted or 1,2-disubstituted olefins in the presence an alcohol; Reaction Sequence G illustrates the selective oxidation of an aliphatic olefin in the presence of an aryl alkane; and Reaction Sequence H demonstrates the selective oxidation of a primary alkyl halide in the presence of an aliphatic olefin.

SELECTIVITY OF THE CHOSEN OXIDIZING AGENTS IN ANALYTE MIXTURES

Reaction A: Oxidation of epoxides in the presence of primary alcohols wherein R, R' and R" are selected from the group consisting of hydrogen and any alkyl or aryl group.

Reaction B: Oxidation of 1,2-diols in the presence of monohydroxy alcohols wherein R and R' are selected from the group consisting of hydrogen and any alkyl or aryl group.

Reaction C: Oxidation of secondary alcohols in the presence of primary alcohols wherein R and R' are selected from the group consisting of hydrogen and any alkyl or aryl group.

Reaction D: Another oxidation of a secondary alcohol in the presence of a primary alcohol wherein R and R' are selected from the group consisting of hydrogen and any alkyl or aryl group.

Reaction E: Oxidation of a primary alcohol in the presence of a secondary alcohol wherein R and R' are selected from one group consisting of hydrogen and any alkyl or aryl group.

Reaction F: Oxidation of monosubstituted or 1,2-disubstituted olefins in the presence of an alcohol wherein R and R' are any other alkyl or aryl group.

Reaction G: Oxidation of an aliphatic olefin in the presence of an aryl alkane wherein R and R' are selected from the group consisting of hydrogen, and any akyl or aryl group.

Reaction H: Oxidation of primary alkyl halide in the presence of an aliphatic alcohol wherein R and R' are hydrogen, carbon and any other compound.

Within the improved apparatus of the present invention the step of selectively oxidizing the analyte of interest is preferably accomplished using a dry/solid format rather than the traditional wet/liquid chemistry procedures. The novel apparatus utilizes an oxidizing pad composed of a porous, chemically inert material such as polyethylene as the matrix. The chosen solid oxidizing agent is then combined with the pad material to form the oxidative reagent pad which is employed as a component part in the novel apparatus. For illustrative purposes only, a detailed description of the preferred protocol for the preparation of a solid oxidizing reagent pad containing periodic acid is provided.

Initially, 20 grams of periodic acid [Aldrich Chemical Company] is placed in a 250 ml filter flask and combined with 100 milliliters of deionized water. This liquid mixture is stirred at room temperature until all the solids have dissolved. The polyethylene pads and liquid mixture are then combined and are stirred vigorously via a magnetic stirrer. As the stirring is performed, a vacuum is applied to the solution and pads, during which air bubbles will evolve from the liquid and from the pores of the pad material. When a sufficient vacuum has been reached [about 20 torr] the vacuum is then released, at which time the majority of the pads will have been imbibed with the liquid mixture. This procedure of application and release of vacuum is repeated until all pads have been imbibed, normally 5–10 iterations. Subsequently, the pads are filtered from the solution using a narrow-stem glass funnel and allowed to drain at room temperature for approximately 20 minutes. Afterwards, they are preferably transferred to a crystalizing dish and placed under vacuum without heat overnight. The pads are then preferably removed to a sealable container and stored in the presence of a dessicant such as silica gel until required for use. In some cases the periodic acid reagent pads can be prepared from aqueous solutions of periodic acid containing either an inorganic or organic acid additive.

The Derivatizing Agent

Once the oxidized product (having at least one carbonyl group available for reaction) has been produced by reacting the analyte of interest in the sample with the selective oxidizing agent, the oxidized product is combined with a derivatizing agent to yield a condensation reaction product formed as a plurality of nucleating sites in-situ. The derivatizing agent is thus a compound capable of providing multiple nucleating particles after reactive contact with the carbonyl containing oxidized product; the derivatizing agent is desirably a chemical composition containing a reactive amine which is deposited onto the surface of a solid substrate. The goal and purpose of the derivatizing agent, therefore, is to react with the oxidized reaction product of the analyte of interest and to provide, thereby, a series of nucleating sites formed in-situ for the subsequent formation and growth of optically visible crystals.

It is most desirable that the derivatizing agent appear on the surface of the solid substrate as a substantially monodispersed system of particles having a size in the micron and submicron range. The use of such derivatizing agents as films of monodispersed particles for subsequent combination and reaction with metastable supersaturated solutions for the detection and identification of small crystals has been described [Vonnegut, B., Science 116;300–301(1952); U.S. Pat. No. 4,380,587]. A representative, but non-exhaustive listing of a derivatizing agents useful with the present invention include the following: 2,4-dinitrophenylhydrazine; semicarbazide; dimethone or dimedone; p-nitrophenylhydrazine; phenylhydrazine; thiosemicarbazide; oximes; bromobenzohydrazine; 2,4-dinitromethylphenylhydrazine; p-carboxyphenylhydrazine; nitrobenzenesulfonhydrazine; nitrobenzohydrazine; diphenylhydrazine; 2-naphthylhydrazine; p-chlorobenzohydrazine; m-chlorobenzohydrazine; nitroguanylhydrazine; alpha-(alpha,4-nitrophenyl)alpha-methylhydrazine; xenylsemicarbazide; tolylsemicarbazide; phenylsemicarbazide; 1-naphphylsemicarbazide; 2-naphphylsemicarbazide; 3,5-dinitrophenylsemicarbazide; dibromomethone; benzothiazole; benzothiazoleine; hydantoins; aminomorpholines; hydrazinobenzoic acid; 5-(1-phenylmethyl) semioxazide; 1,3-cyclohexadione; 1,2-bis(p-methoxybenzylamino)ethane; adipic dihydrazide; benzoylhydrazine; isonicotinic acid hydrazide; nicotinic acid hydrazide; oxalyl dihydrazide; oxamic hydrazide; and salicylhydrazide. The preferred dervatizing agents for the method of the present invention are listed by Table III hereinafter.

The derivatizing agent used in the present invention preferably is a dispersion of particles substantially of the same size which is retained on the surface of a solid substrate with relatively uniform spacing between them, the particles preferably ranging from about 0.1–1.0 micrometers in size. It will be noted also that a single derivatizing agent may be useful for reaction with a variety of different oxidized products in either vaporized or liquid physical states—each of which will react with the chosen derivatizing agent to form a plurality of immobilized nucleating sites in-situ on the surface of the solid substrate. It will be understood that the nucleating sites formed in-situ are themselves crystals which are invisible to the unaided eye but which serve as specific initiation sites for the subsequent formation and growth of optically detectable crystals.

A film of monodispersed particles comprising the chosen derivatizing agent may be conveniently prepared by directing an aerosol of the solution comprising the derivatizing agent against the surface of a solid substrate in the conventionally known manner. By maintaining very accurate control over the concentration in the aerosol over time and by controlling the speed of delivery of the aerosol to the surface of the solid substrate, one may deposit an accurately controlled amount of the derivatizing agent onto the surface. To obtain satisfactory adherence of the aerosol particles to the surface of the solid substrate, it is often desirable (but not necessary) to pretreat the surface by application of an electrostatic charge and/or heating the aerosol. Equipment for forming the aerosol in the desired range of particles is commercially available.

It should be noted also that the solid substrate upon which the chosen derivatizing agent is located may be shaped into a variety of different forms and configurations. The preferred format will be described in the detailed description for the improved apparatus comprising the present invention. Nevertheless, a variety of differently configured apparatus and articles may be prepared as test kits and film badges which employ the derivatizing agent in the described manner for the purpose of forming a plurality of immobilized nucleating sites in-situ.

ity of immobilized nucleating sites are preferably treated with a selective, metastable supersaturated (developer) solution such that a plurality of optically detectable crystals are formed on the surface of the solid substrate. The metastable supersaturated solution is an aqueous or non-aqueous liquid containing a supersaturated concentration of a crystal growing chemical composition which is both chemically and physically stable for a defined period of time. This solution also provides an additional point of selective control such that crystal formation and growth will occur only in the presence of the analyte of interest. Accordingly, when the metastable supersaturated (developer) solution is combined with the nucleating sites formed in-situ on the surface of the solid substrate, crystallization will occur at each of the individual nucleating sites resulting in the formation and growth of optically detectable crystals. A useful but non-exhaustive listing of selective metastable supersaturated (developer) solutions is provided by Table III. Each developer solution is correlated with a preferred derivatizing agent, a specific analyte of interest, and the preferred oxidized reaction product of that analyte. The quantities of each chemical composition and the manner of utilizing each particular chemical composition to prepare a metastable supersaturated (developer) solution in aqueous and non-aqueous liquids are conventionally known in the art.

It is noteworthy that the listing of Table III indicates that the composition of the metastable supersaturated solution is preferably identical to the condensation reaction product formed by the reaction of the oxidized analyte and the derivatizing agent. It is specifically

TABLE III

| Analyte | Carbonyl of Choice Formed by Oxidation | Preferred Derivatizing Agent | Selective Metastable Supersaturated Developer Solution |
|---|---|---|---|
| Epoxides | | | |
| Ethylene oxide | Formaldehyde | p-hydroxybenzoic acid hydrazide | formyl-p-hydroxybenzoic acid hydrazone |
| Epichlorohydrin | Chloroacetaldehyde (formaldehyde) | Semicarbazide | Chloroacetyl semicarbazone |
| Alcohols | | | |
| 2-butoxyethanol | 2-butoxyacetaldehyde | semicarbazide | 2-butoxyacetyl semicarbazone |
| Butyl alcohol | Butyraldehyde | p-hydroxybenzoic acid hydrazide | Butyrl-p-hydroxybenzoic acid hydrazone |
| Cyclohexanol | Cyclohexanone | 2,4-dinitrophenyl hydrazine | cyclohexanone-2,4-dinitro phenylhydrazone |
| Isopropyl alcohol | Acetone | 2,4-dinitrophenyl hydrazine | acetone-2,4-dinitro phenylhydrazone |
| Methyl cellosolve | Methoxy acetaldehyde | Semicarbazide | Methoxyacetyl semicarbazone |
| Olefins (Double Bonds) | | | |
| Styrene | Benzaldehyde | 2,4-dinitrophenyl hydrazine | Benzaldehyde 2,4-dinitro phenylhydrazone |
| Ethylene | Acetaldehyde | p-hydroxybenzoic acid hydrazide | Acetyl-p-hydroxybenzoic acid hydrazone |
| Aryl Alkanes | | | |
| p-xylene | Terephthaldehyde | 2,4-dinitrophenyl hydrazine | Terepthaldehyde 2,4-dinitro phenyl hydrazone |
| m-chlorotoluene | m-chlorobenzaldehyde | 2,4-dinitrophenyl hydrazine | m-chlorobenzaldehyde 2,4-dinitrophenyl hydrazone |
| Primary Alkyl Halides | | | |
| Alkyl chloride | Acrolein | Semicarbazide | Acrolein semicarbazone |
| Propyl bromide | Propionaldehyde | p-hydroxybenzoic acid hydrazide | Propionyl p-hydroxybenzoic acid hydrazone |

The Metastable Supersaturated (Developer) Solution

Once the nucleating sites have been formed in-situ on the surface of a solid substrate via the reaction of the oxidized product with the derivatizing agent, the pluralnoted that under certain circumstances, the chemical composition of the metastable supersaturated solution need not be chemically identical to the condensation product forming the individual nucleating sites, but may be distinctly different in chemical formula and structure while remaining sufficiently similar for crystalization to occur—a phenomenon termed "epitaxy." For purposes of the present invention, it is preferred that the chemical composition of the substance used to prepare the metastable supersaturated (developer) solution be identical in each and every instance to the condensation product forming the individual nucleating sites on the solid substrate in order to provide a point of selectivity and control by which to distinguish an individual analyte of interest from a closely analogous chemical entity. To demonstrate this selective control provided by the composition of the metastable, supersaturated solution, an illustrative example for the detection of propylene oxide in the presence of ethylene oxide is provided as seen by the following series of reactions.

posed of acetyl-p-hydroxybenzoic acid hydrazone will be grown into optically detectable crystals while the nucleating sites composed of formyl-p-hydroxybenzoic acid hydrazone remain invisible to the naked eye. Accordingly, so long as the composition of the metastable supersaturated (developer) solution in this instance is solely acetyl-p-hydroxybenzoic acid hydrazone, only the individual nucleating sites uniquely attributable to the presence of the analyte of interest, propylene oxide, will be grown as optically visible and distinguishable crystals despite the concomitant presence of ethylene oxide in the initial test sample.

It is noteworthy that the size and nature of the crystals formed and grown on the surface of the solid substrate as a result of the treatment with the selective For purposes of the illustrative example only, an oxidizing agent, periodic acid, is purposefully employed which is not sufficiently selective in this instance to discriminate between the analyte of interest, propylene oxide, and its homolog, ethylene oxide. Under these test conditions, the oxidation of propylene oxide will yield one molecule of formaldehyde and one molecule of acetaldehyde. The oxidation of the ethylene oxide in the same reaction mixture will yield two molecules of formaldehyde. After reaction with the derivatizing agent, p-hydroxybenzoic acid hydrazide, two different condensation reaction products are formed as individual nucleating sites immobilized on the surface of the substrate. The formaldehyde (regardless of origin) reacts with the derivatizing agent to form formyl-p-hydroxybenzoic acid hydrazone as the condensation reaction product. The acetaldehyde reacts with the derivatizing agent to form acetyl-p-hydroxybenzoic acid hydrazone as the other condensation reaction product. By requiring the composition of the metastable, supersaturated (developer) solution to be identical with the condensation reaction product formed by the analyte of interest—the propylene oxide—only the nucleating sites comdeveloper solution are directly affected by the individual number of nucleating sites formed in-situ by the interaction of the oxidized product and the derivatizing agent. Relatively speaking, if the oxidation reaction releases only a small quantity of oxidized analytes of interest, relatively few nucleating sites are formed of the surface of the solid; alternatively, if the oxidation step produces a relatively large quantity of oxidized product, a proportionately larger number of individual nucleating sites will be formed on the surface of the solid. The number of nucleating sites formed will determine the ultimate size of the crystals grown since the amount of crystallizable material in the developer solution will be divided equally among all the nucleating sites which are identical in chemical composition regardless of their number. Accordingly, if a large number of nucleating sites are present, the quantity of crystallizing compound in the developer solution will be distributed over a greater number of nucleating sites and the size of each crystal formed and grown will be relatively small. Conversely, if the number of nucleating sites formed is relatively small, the same concentration of crystallizable material in the developer solution will be equally distributed over a smaller number of individual nucleating sites, thereby causing a greater quantity of crystallizable material to be deposited on each site. This causes the formation of larger sized crystals.

Quantitatively therefore, the concentration of the crystalizable matter comprising the metastable, supersaturated (developer) solution is important in that the concentration be of sufficient magnitude to provide for the growth of optically detectable crystals—even when that number of individual nucleating sites is at a maximum. For this reason, metastable supersaturated (developer) solutions are preferably prepared at a concentration ranging from 2-10 times saturation concentration. By using developer solution of such concentration magnitude, metastable solutions, rapid crystal formation and growth will occur after one or two minutes contact with the individual nucleating sites. In this manner, the speed of the assay methodology is maintained, and maximum crystal growth is obtained within 5-10 minutes; and is visibly complete in all respects in not more than 60 minutes time.

It should also be recognized that the control of the speed of matter deposition also directly affects the ability of the grown crystals to be optically detected. For example, a rapid deposition of crystallizable material from the developer solution onto the individual nucleating sites tends to build up the crystal face toward an irregular point; whereas more leisurely deposition of crystallizable material produces a crystal line lattice whose crystal face is essentially flat. Optically, light is scattered more readily from crystals which have irregular and pointed faces and thus become more "visible" as a result of the light scattering effect; in comparison, flat-faced crystal lattices scatter light minimally and are more difficult to visualize with the unaided eye or with the use of specific crystal detection equipment. For this reason also, it is preferred that the concentration of the chemical compositions used in making metastable supersaturated (developer) solution be as concentrated as possible in order to promote rapid deposition of the crystalline material when brought into reactive contact with the individual nucleating sites.

In view of the inherent instability of a supersaturated solution prepared in maximum concentration, it is advisable to prepare the developer solution immediately prior to use. Furthermore, stabilizers such as polyvinyl alcohol, polyvinyl pyrrolidone, gelatin, agar, sodium carboxymethyl cellulose, methyl and ethyl cellulose and the like are useful and desirable for prolonging the effective life of the supersaturated developer solution in the present invention. As a practical matter therefore, it is convenient to have two prepared reagents available, one or both of which is in solution, which may be mixed at a predetermined ratio on-site to form the metastable supersaturated (developer) solution. The mixed solution may then be combined with the individual nucleating sites immobilized on the surface of the solid substrate to form the optically detectable crystals.

The effect of forming and growing crystals in this manner gives rise to an optically observable and detectable change which is both a qualitative and quantitative measure of the analyte of interest in the test sample. The degree of optically detectable crystals provides both a qualitative and/or quantitative measure which is correlatable with a calculated amount of an analyte of interest in the fluid sample. Typically, quantitative results in the parts per million range or less may be reproducibly obtained within 10-15 minutes by the formation and growth of optically detectable crystals in the heretofor described manner. For best quantitative results, it is preferred that an optical measurement (such as diffuse reflection) be utilized as a correlation for calculating the quantity of the analyte of interest in the initial test sample.

The Improved Apparatus of the Present Invention

Figure 1:
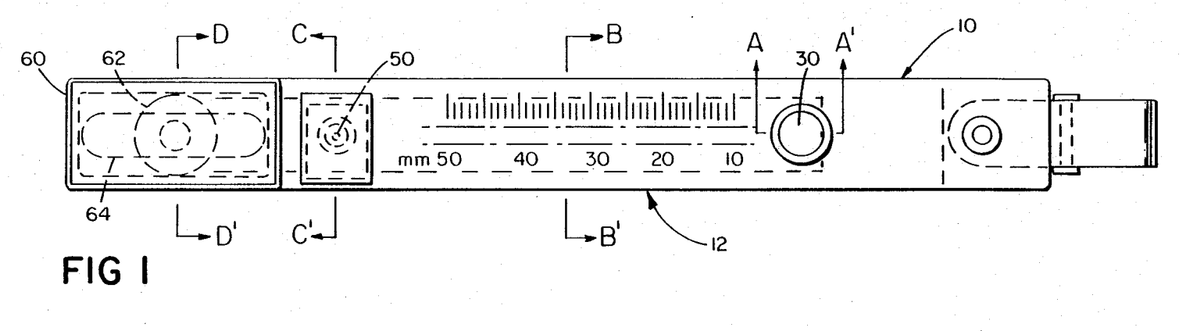
FIG. 1 is an overhead view of a preferred film badge apparatus.
Figure 2:
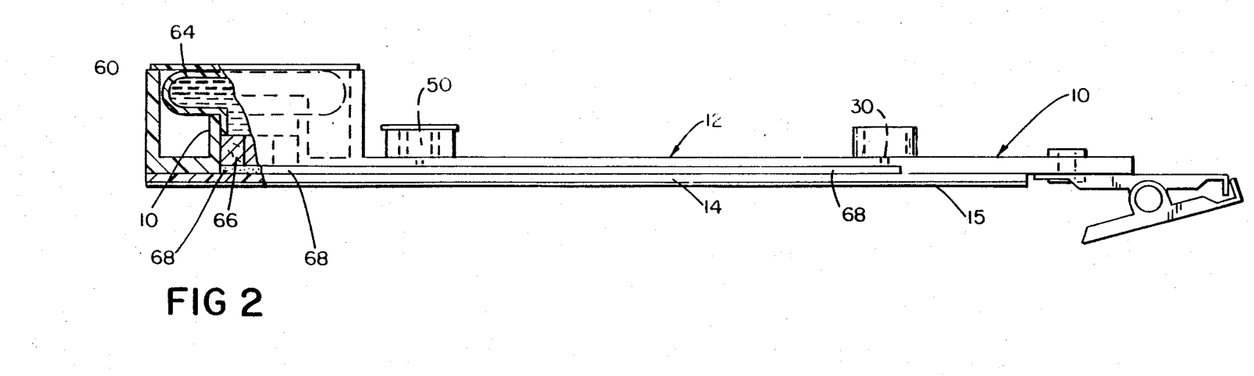
FIG. 2 is a side-view of the apparatus illustrated by FIG. 1, partly in cross-section.
Figure 3:
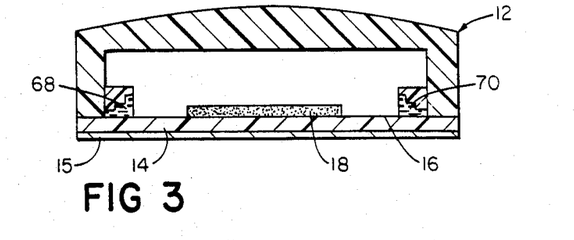
FIG. 3 is a cross-sectional view of the embodiment illustrated in FIG. 1 along the axis BB'.

The manipulative steps previously described herein are preferably performed in an improved apparatus such as the monitoring badge device illustrated by FIGS. 1-10, respectively. As shown therein, preferred embodiments of the improved apparatus provide a chamber 10 preferably in the form of a rigid one-piece molded transparent plastic article illustrated in overhead and side views by FIGS. 1 and 2, respectively. The chamber 10 is preferably made of a resilient and transparent material such as polystyrene or polycarbonate resin having a closed interior volume which is divided into individual sections and spaces of differing configuration and volume. The interior of the chamber 10 is divided into a U-shaped section 12, a reagent housing 30, a developer solution inlet 50, and an enclosed receptacle 60. A plastic sheet 14 forms a common back wall throughout the entirety of the chamber 10 and preferably has a metallized layer 15 bonded to the exterior surface to aid in visualization of the crystals to be formed subsequently in the chamber. As shown in FIG. 3, the interior surface 16 of the sheet 14 within the U-shaped section 12 acts as the solid substrate upon which is a derivatizing agent 18 is deposited. It is most desirable to closely control the precise dimensions and configuration of the U-shaped section 12 in order to obtain accurately reproducible results. The dimensions and configuration may vary within limits depending upon the specific analyte of interest to be detected, the chosen derivatizing agent, the metastable supersaturated solution to be employed, and the range of concentrations and time of exposure to be accommodated. In most instances, the void dimensions above the interior surface 16 of the sheet 14 has a width in the range of 0.2-1.0 inches and has a height of approximately of 0.005-0.03 inches.

Figure 4:
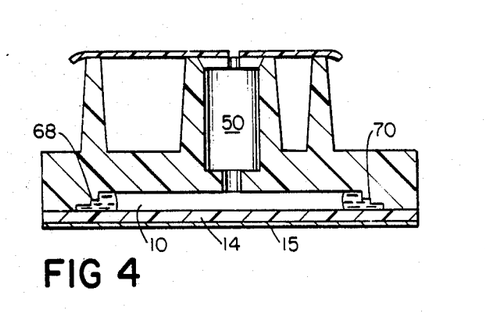
FIG. 4 is a cross-sectional view of the embodiment illustrated in FIG. 1 along the axis CC'.

As seen in FIG. 4, the developer solution inlet 50 is integrally joined to the U-shaped section 12 and provides means for introduction of the metastable, supersaturated solution into the interior of the chamber 10 such that it can be applied to the interior surface 16 of the sheet 14 in a controlled manner on demand. The developer solution inlet 50 is to be sealed with impervious tape which is removed when the developer solution is introduced.

Figure 5:
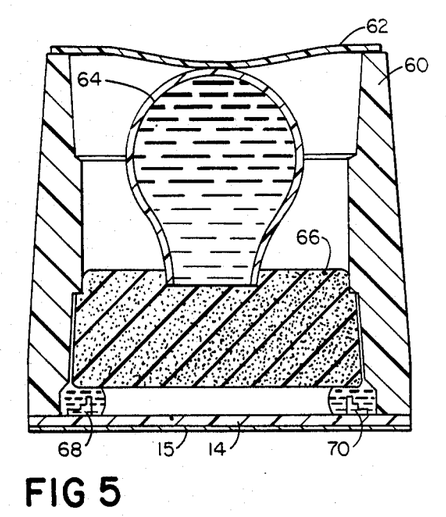
FIG. 5 is a cross-sectional view of the embodiment illustrated in FIG. 1 along the axis DD'.

As seen in FIG. 5, the enclosed receptacle 60 is composed of a retainer 62 and a frangible ampule 64 filled with an aqueous salt solution of choice. The receptacle 60 is sealed by the retainer 62, a strip of flexible impervious adhesive tape adhering at its outer margins to the receptacle. Beneath the frangible ampule 64 is a sponge material 66 which is in fluid communication with a pair of capillary openings 68 and 70 at the bottom of the receptacle 60. The capillary openings 68, 70 extend through the interior of chamber 10 along the longitudinal margins serve as capillary channels or troughs for the flow of the aqueous salt solution from the receptacle 60 through the U-shaped section 12. This salt solution serves to maintain a constant relative humidity within the chamber 10. If desired, strips of wicking fibrous or porous material may be placed within the capillary openings 68 and 70 to aid in maintaining a uniform flow of liquid.

Figure 6:
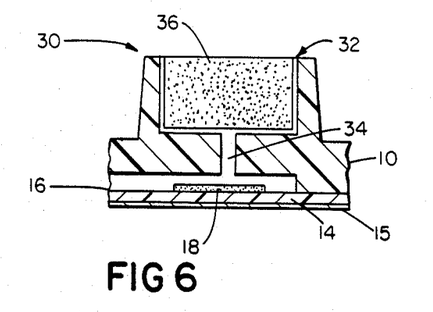
FIG. 6 is a cross-sectional view on an enlarged scale of one preferred embodiment illustrated by FIG. 1 along the axis AA'.
Figure 7:
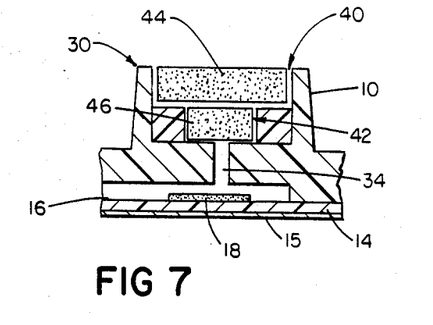
FIG. 7 is cross-sectional view on an enlarged scale of another preferred embodiment of the apparatus of FIG. 1 along the axis AA'.

The reagent housing 30 is shown in alternative embodiments by FIGS. 6 and 7, respectively. As seen in Fig. 6, the reagent housing 30 is configured as a substantially cylindrical space, is occupied by an oxidizing reagent pad 36 which preferably comprises a polyethylene pad matrix containing the chosen oxidizing agent for reaction with the analyte of interest in the sample. It is intended that the oxidizing reagent pad 36 substantially fill the entirety of the space 32 such that any liquid or gaseous initial test sample cannot avoid passing through the porous matrix of the pad material before entering the narrow passage 34 and gaining entry into the interior of the U-shaped section 12. The alternate preferred embodiment of the reagent housing 30 is illustrated by FIG. 7 in which the internal volume has been divided into an upper spaced region 40 and a lower spaced region 42, after which the volume narrows into the passage 34 for further communication with the interior of the chamber 10. In this embodiment, the upper spaced region 40 is occupied by a dry cleansing reagent pad 44 preferably composed of a porous polyethylene pad matrix material containing the chosen cleansing agent. Lying immediately adjacent to this cleansing reagent pad 44 is an oxidizing reagent pad 46 of smaller volume which substantially fills and occupies the lower spaced region 42. It is intended and expected that the cleansing reagent pad 44 fill the upper spaced region 40 such that a fluid sample entering the chamber 10 through the reagent housing 30 must first enter and pass through the cleansing reagent pad 44 and also pass through the adjacently positioned oxidizing reagent pad 46 filling the lower spaced region 42 before entering the remainder of the interior of chamber 10 through one narrow passage 34. In this manner, a fluid sample containing the analyte of interest will react with both the cleansing agent of the reagent pad 44 and subsequently with the oxidizing agent of the reagent pad 46 in the proper reaction sequence.

To prepare the apparatus for intended use, the film badge is exposed to the ambient environment by removing the device from a sealed package. The fragile ampule is broken and the aqueous salt solution flows through the capillaries 68, 70. After the apparatus is exposed to either a gaseous or liquid sample for a predetermined period of time, it is intended that the analyte of interest will have passed through the reagent housing 30 and reacted with both the cleansing agent residing within the cleansing reagent pad 44 followed by subsequent reaction with the oxidizing agent residing within the oxidizing reagent pad 46. The oxidized product containing at least one carbonyl group for reaction is preferably released from the oxidizing reagent pad 46 in vaporized gaseous form which then travels through the narrow passage 34 and enters the interior of the U-shaped section 12. Once within the U-shaped section 12, the vaporized oxidized product will react with the derivatizing agent 18 present in solid microparticle form to yield a condensation reaction product formed as a plurality of nucleating sites in-situ on the interior surface 16 of the sheet 14. After a predetermined time for reaction has elapsed, a metastable supersaturated solution is introduced via the developer solution inlet 50 and fills the U-shaped section 12 for reaction with the condensation reaction product formed as the plurality of nucleating sites in-situ. The treatment of these nucleating sites with the selective metastable supersaturated solution forms a plurality of optically detectable crystals on the interior surface 16 of the sheet 14. The presence of these optically detectable crystals serves as a qualitative and/or quantitative measure of the analyte of interest in the initial test sample.

Figure 8:
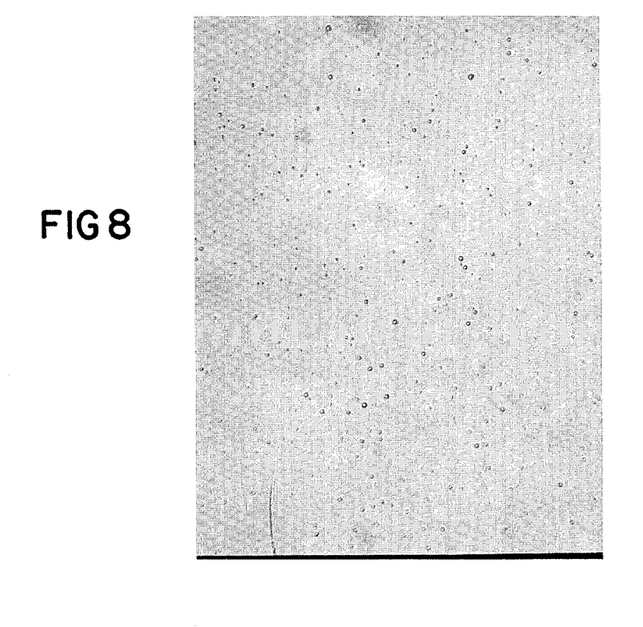
FIG. 8 is a photograph illustrating the derivatizing agent on the surface of the solid substrate in the embodiment of FIG. 1.
Figure 9:
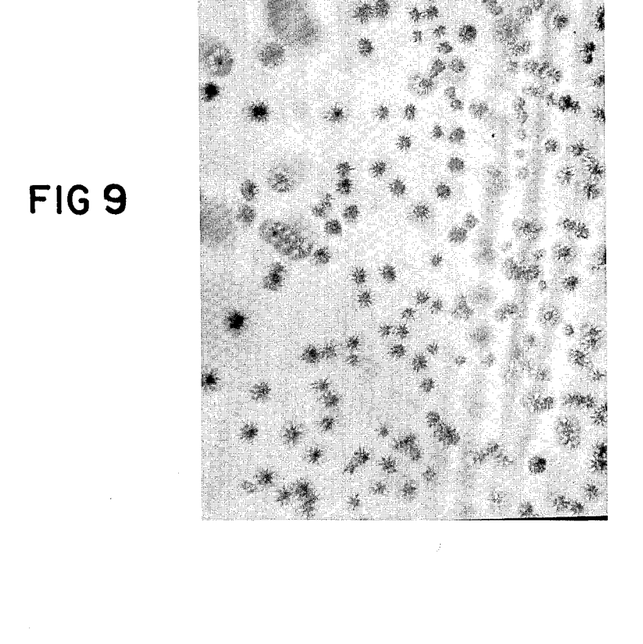
FIG. 9 is a photograph of the optically detectable crystals grown on the surface of the solid substrate in the embodiment of FIG. 1.
Figure 10:
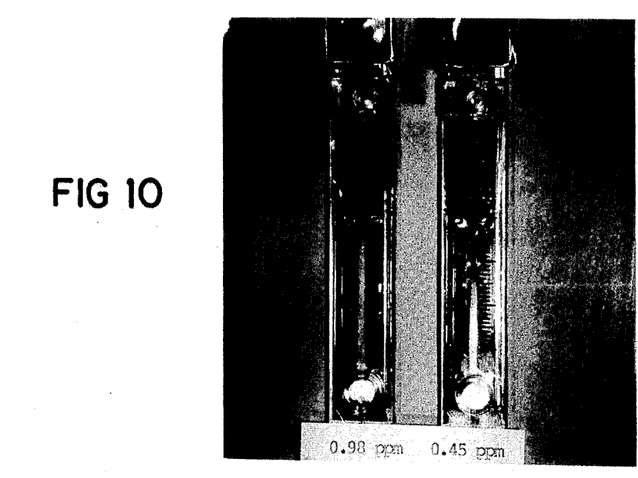
FIG. 10 is a photograph illustrating quantitative difference in the detection of ethylene oxide using the embodiments of FIG. 1.

The utility and operability of this improved apparatus design and configuration is illustrated by FIGS. 8, 9, and 10, respectively. FIG. 8 illustrates a magnified view (300×) of the derivatizing agent 18 deposited on the interior surface 16 of the sheet 14 within the U-shaped section 12 before any reactions have occurred. Fig. 9 is a magnified view (300×) demonstrating the formation of optically detectable crystals on the surface 16 after the apparatus has been exposed to a sample for a predetermined period of time and the manipulated steps of the present methodology have been performed within this apparatus. FIG. 10 demonstrates the ability to quantitatively detect and differentiate between alternate concentrations of an analyte of interest, ethylene oxide, using the methodology of the present invention after the apparatus and sample have been in contact for a period of approximately 8 hours duration. The apparatus on the left within FIG. 10 reveals a sample which contains 0.98 parts-per-million to be present within the sample whereas the article on the right of FIG. 10 demonstrates that its test sample contained only 0.45 parts-per-million of ethylene oxide over the same exposure period. A scale of arbitrary units can be calibrated as to enable the user to quickly determine the concentration of the analyte in the sample.

The present invention is not to be restricted in form nor limited in scope except by the claims appended hereto.

What we claim is:

1. A rapid method for detecting the presence of an analyte of interest in a fluid sample, said method comprising the steps of:

reacting the fluid sample with an oxidizing agent selectively reactive with the analyte of interest to yield at least one oxidized product having at least one carbonyl group available for reaction;

combining said oxidized product with derivatizing agent in the presence of a solid support to yield a reaction product formed as a plurality of nucleating sites in-situ, said nucleating sites being immobilized on the surface of a solid substrate;

reacting said immobilized nucleating sites with a metastable supersaturated solution such that a plurality of optically detectable crystals are formed; and optically detecting the presence of said formed crystals as a measure of the analyte of interest in the sample.

2. A rapid method for detecting the presence of an analyte of interest in a fluid sample, said method comprising the steps of:

reacting the fluid sample in the ambient environment with a solid oxidizing agent reactive with the analyte of interest to yield at least one oxidized product having at least one carbonyl group available for reaction;

combining said oxidized product with a derivatizing agent in the presence of a solid support to yield a reaction product formed as a plurality of nucleating sites in-situ, said nucleating sites being immobilized on the surface of a solid substrate;

reacting said immobilized nucleating sites with a metastable supersaturated solution such that a plurality of optically detectable crystals are formed; and optically detecting the presence of said formed crystals as a measure of the analyte of interest in the sample.

3. A method for converting an analyte of interest in a mixed fluid sample into a carbonyl-containing composition in the presence of at least one other substance, said method comprising the steps of:

combining the fluid sample with a cleansing agent which selectively reacts with the other substance and is substantially unreactive with the analyte of interest to yield a cleansed sample substantially free of the other substance; and reacting said cleansed sample with a selective oxidizing agent reactive with the analyte of interest to yield at least one oxidized product having at least one carbonyl group available for reaction.

4. A method for converting an analyte of interest in a mixed fluid sample into a carbonyl-containing composition in the presence of at least one other substance, said method comprising the steps of:

combining the fluid sample with a cleansing agent which selectively reacts with the other substance and is substantially unreactive with the analyte of interest to yield a cleansed sample substantially free of the other substance; and reacting said cleansed sample with a solid oxidizing agent reactive with the the analyte of interest to yield at least one oxidized product having at least one carbonyl group available for reaction.

5. A rapid method for detecting an analyte of interest in a mixed fluid sample containing at least one other substance, said method comprising the steps of;

combining the mixed fluid sample with a cleansing agent which reacts selectively with the other substance and is substantially unreactive with the analyte of interaest to yield a cleansed sample substantially free of the other substance;

reacting said cleansed sample with an oxidizing agent selectively reactive with the analyte of interest to yield at least one oxidized product having at least one carbonyl group available for reaction;

combining said oxidized product with a derivatizing agent in the presence of a solid support to yield a reaction product formed as a plurality of nucleating sites in-situ, said nucleating sites being immobilized on the surface of a solid substrate;

reacting said immobilized nucleating sites with a metastable supersaturated solution such that a plurality of optically detectable crystals are formed; and optically detecting the presence of said formed crystals as a measure of the analyte of interest in the sample.

6. A rapid method for detecting an analyte of interest in a mixed fluid sample containing at least one other substance, said method comprising the steps of:

combining the mixed fluid sample with a cleansing agent which reacts selectively with the other substance and is substantially unreactive with the analyte of interest to yield a cleansed sample substantially free of the other substance;

reacting said cleansed sample with a solid oxidizing agent reactive with the analyte of interest to yield at least one oxidized product having at least one carbonyl group available for reaction;

combining said oxidized product with a derivatizing agent in the presence of a solid support to yield a reaction product formed as a plurality of nucleating sites in-situ, said nucleating sites being immobilized on the surface of a solid substrate;

reacting said immobilized nucleating sites with a metastable supersaturated solution such that a plurality of optically detectable crystals are formed;

optically detecting the presence of said formed crystals as a measure of the analyte of interest in the sample.

7. The method as recited in claim 1, 2, 3, 4, 5, or 6 wherein the analyte of interest is an entity selected from the group consisting of epoxides, alcohols, olefins, aryl alkanes and primary alkyl halides.

8. The method as recited in claim 1, 2, 3, 4, 5, or 6 wherein said oxidizing agent is selected from the group consisting of periodic acid, manganese dioxide, 3-carboxypyridinium dichromate, potassium permanganate, ceric ammonium nitrate, palladium chloride and cupric chloride, and 4-dimethylaminopyridinen-N-oxide.

9. The method as recited in claim 3, 4, 5, or 6 wherein the other substance is an entity selected from the group consisting of aldehydes and ketones.

10. The method as recited in claim 9 wherein said cleansing agent is selected from the group consisting of nicotinic acid hydrazide, 2,4-dinitrophenyl hydrazine, salicylhyrazide, and p-hydroxybenzoic acid hydrazide.

11. The method as recited in claim 3, 4, 5, or 6 wherein the other substance is an entity selected from the group consisting of organic acids and inorganic acids.

12. The method as recited in claim 11 wherein said cleansing agent is selected from the group consisting of alkali and alkaline earth hydroxides, carbonates, and bicarbonates.

13. The method as recited in claim 3, 4, 5, or 6 wherein the other substance is an entity selected from the group consisting of ammonia and amines.

14. The method as recited in claim 13 wherein said cleansing agent is an organic acid.

15. The method as recited in claim 3, 4, 5, or 6 wherein the other substance is a cyanide.

16. The method as recited in claim 15 wherein said cleansing agent is an entity selected from the group consisting of silver salts, nickel salts, copper salts and iron salts.

17. The method as recited in claim 1, 2, 5, or 6 wherein said derivatizing agent is selected from the group consisting of adipic dihydrazide; benzoylhydrazine; isonicotinic acid hydrazide; nicotinic acid hydrazide; oxalyl dihydrazide; oxamic hydrazide; salicylhydrazide; 2,4-dinitrophenylhydrazine; semicarbazide; dimethone or dimedone; p-nitrophenylhydrazine; phenylhydrazine; thiosemicarbazide; bromobenzohydrazine o,m,p); 2,4-dinitromethyphenylhydrazine; p-carboxphenylhydrazine; nitrobenzenesulfonhydrazine; p-nitrobenzohydrazine; diphenylhydrazine; 2-naphthylhydrazine; p-chlorobenzohydrazine; m-chlorobenzohydrazine; nitroguanylhydrazine; alpha-(alpha 4-nitrophenyl)-alpha-methyl-hydrazine; xenylsemicarbazide; tolylsemicarbazide (o,m,p); phenylsemicarbazide; 1-naphthylsemicarbazide; 2-naththylsemicarbazide; 3,5-dinitrophenylsemicarbazide; dibromomethone; benzothiazole; benzothiazoline; aminomorpholines; hydrazinobenzoic acid; 5-(1-phenylmethyl)semioxazide 1,3-cyclohexadione; 1,2-bis(p-methoxybenzylamino)ethane or p-hydroxybenzoic acid hydrazide.

18. The method as recited in claim 1, 2, 5, or 6 wherein said metastable supersaturated solution is a carbonyl-reaction product of adipic dihydrazide; benzoylhydrazine; isonicotinic acid hydrazide; nicotinic acid hydrazide; oxalyl dihydrazide; oxamic hydrazide; salicylhydrazide; 2,4-dinitrophenylnydrazine; semicarbazide; dimethone or dimedone; p-nitrophenylhydrazine; phenylhydrazine; thiosemicarbazide; bromobenzohydrazine o,m,p); 2,4-dinitromethylphenylhydrazine; p-carboxphenylhydrazine; nitrobenzenesulfonhydrazine; p-nitrobenzohydrazine; diphenylhydrazine; 2-naphthylhydrazine; p-chlorobenzohydrazine; m-chlorobenzohydrazine; nitroguanylhydrazine; alpha-(alpha,4-nitrophenyl)-alpha-methyl-hydrazine; xenylsemicarbazide; tolylsemicarbazide (o,m,p); phenylsemicarbazide; 1-naphthylsemicarbazide; 2-naththylsemicarbazide; 3,5-dinitrophenylsemicarbazide; dibromomethone; benzothiazole; benzothiazoline; aminomorpholines; hydrazinobenzoic acid; 5-(1-phenylmethyl)semioxazide 1,3-cyclohexadione; 1,2-bis(p-methoxybenzylamino)ethane or p-hydroxybenzoic acid hydrazide.

19. The method as recited in claim 1, 2, 5, or 6 wherein said metastable supersaturated solution comprises a selective composition which is identical to said reaction product formed by said oxidized product with said derivatizing agent.

20. An apparatus for the detection of an analyte of interest in a fluid sample, said apparatus comprising:
a chamber having a closed interior volume and means for entry of the fluid sample into the interior of said chamber;
oxidizing reagent means within said chamber for selective reaction with the analyte of interest in the sample to yield at least one oxidized product having at least one carbonyl group available for reaction;
a solid substrate within said chamber adjacent to said selective oxidizing reagent means, a surface of said solid substrate supporting a derivatizing agent able to react with such oxidized product as is present within the interior of said chamber to yield a reaction product formed as a plurality of immobilized nucleating sites in-situ on the surface of said solid substrate;
means for treating said solid substrate with a metastable supersaturated solution such that said nucleating sites on the surface of said substrate form a plurality of optically detectable crystals; and
means for optically detecting the presence of said crystals on the surface of said solid substrate as a measure of the analyte of interest in the sample.

21. An apparatus for the detection of an analyte of interest in a fluid sample, said apparatus comprising:
a chamber having a closed interior volume and means for entry of the fluid sample into the interior of said chamber;
solid oxidizing reagent means within said chamber for reaction with the analyte of interest in the sample to yield at least one oxidized product having at least one carbonyl group available for reaction;
a solid substrate within said chamber adjacent to said solid oxidizing reagent means, a surface of said solid substrate supporting a derivatizing agent able to react with such oxidized product as is present within the interior of said chamber to yield a reaction product formed as a plurality of immobilized nucleating sites in-situ on the surface of said solid substrate;
means for treating said solid substrate with a metastable supersaturated solution such that said nucleating sites on the surface of said substrate form a plurality of optically detectable crystals; and
means for optically detecting the presence of said crystals on the surface of said solid substrate as a measure of the analyte of interest in the sample.

22. An apparatus for the detection of an analyte of interest in a mixed fluid sample containing at least one other substance, said apparatus comprising:
a chamber having a closed interior volume and a means for entry of the mixed fluid sample into the interior of said chamber;
cleansing reagent means within said chamber for selectively reacting with the other substance in the sample and substantially avoiding reaction with the analyte of interest such that a cleansed sample substantially free of the other substance is obtained;
oxidizing reagent means within said chamber adjacent to said dry cleansing reagent means, said oxidizing reagent means selectively oxidizing the analyte of interest in said cleansed sample to yield at least one oxidized product having at least one carbonyl group available for reaction;
a solid substrate within said chamber adjacent to said dry oxidizing reagent means, a surface of said solid substrate supporting a derivatizing agent able to react with such oxidized product as is present within said chamber to yield a reaction product formed as a plurality of nucleating sites in-situ on the surface of said solid substrate;
means for treating said solid substrate with a metastable supersaturated solution to said solid substrate such that said nucleating sites on the surface of said substrate form a plurality of optically detectable crystals; and
means for optically detecting the presence of said formed crystals on the surface of said solid substrate as a measure of the analyte of interest in the mixed sample.

23. An apparatus for the detection of an analyte of interest in a mixed fluid sample containing at least one other substance, said apparatus comprising:
a chamber having a closed interior volume and means for entry of the mixed fluid sample into the interior of said chamber;
solid cleansing reagent means within said chamber for selectively reacting with the other substance and substantially avoiding reaction with the analyte of interest such that a cleansed sample substantially free of the other substance is obtained;
solid oxidizing reagent means within said chamber adjacent to said solid cleansing reagent means for oxidizing the analyte of interest in said cleansed sample to yield at least one oxidized product having at least one carbonyl group available for reaction;
a solid substrate within said chamber adjacent to said solid oxidizing reagent means, a surface of said solid substrate supporting a derivatizing agent able to react with such oxidized product as is present within said chamber to yield a reaction product formed as a plurality of immobilized nucleating sites in-situ on the surface of said solid substrate;

means for treating said solid substrate with a metastable supersaturated solution such that said nucleating sites on the surface of said substrate form a plurality of optically detectable crystals; and means for optically detecting the presence of said crystals on the surface of said solid substrate as a measure of the analyte of interest in the sample.

24. The apparatus as recited in claim 20, 21, 22, or 23 wherein said oxidizing reagent means comprises a porous material containing an oxidizing agent.

25. The apparatus as recited in claim 22 or 23 wherein said cleansing reagent means comprises a porous material containing a cleansing agent.

26. The apparatus as recited in claim 20, 21, 22, or 23 wherein said chamber is composed of optically transparent material.

27. The apparatus as recited in claim 20, 21, 22, or 23 wherein a quantitative scale is disposed upon said chamber to provide quantitative measurement.

28. The apparatus as recited in claim 20, 21, 22, or 23 wherein said metastable supersaturated solution comprises a selective composition which is identical to said reaction formed by said oxidized product with said derivatizing agent.

29. The apparatus as recited in claim 22 or 23 wherein the other substance is an entity selected from the group consisting of aldehydes and ketones.

30. The apparatus as recited in claim 29 wherein said cleansing reagent means is selected from the group consisting of nicotinic acid hydrazide, 2,4-dinitrophenyl hydrazine, salicylhydrazide, and p-hydroxybenzoic acid hydrazide.

31. The apparatus as recited in claim 22 or 23 wherein the other substance is an entity selected from the group consisting of organic acids and inorganic acids.

32. The apparatus as recited in claim 31 wherein said cleansing reagent means is selected from the group consisting of alkali and alkaline earth hydroxides, carbonates and bicarbonates.

33. The apparatus as recited in claim 22 or 23 wherein the other substance is an entity selected from the group consisting of ammonia and amines.

34. The apparatus as recited in claim 33 wherein said cleansing reagent means is an organic acid.

35. The apparatus as recited in claim 22 or 23 wherein the other substance is a cyanide.

36. The apparatus as recited in claim 35 wherein said cleansing reagent means is selected from the group consisting of silver salts, nickel salts, copper salts, and iron salts.

37. The apparatus as recited in claim 20, 21, 22, or 23 wherein said oxidizing reagent means is selected from the group consisting of periodic acid, manganese dioxide, 3-carboxy pyridinium dichromate, potassium permanganate, palladium chloride and cupric chloride, and 4-dimethylaminopyridine-N-oxide.

38. The apparatus as recited in claim 20, 21, 22, or 23 wherein said derivatizing agent is selected from the group consisting of adipic dihydrazide; benzoylhydrazine; isonicotinic acid hydrazide; nicotinic acid hydrazide; oxalyl dihydrazide; oxamic hydrazide; salicylhydrazide; 2,4-dinitrophenylhydrazine; semicarbazide; dimethone or dimedone; p-nitrophenylhydrazine; phenylhydrazine; thiosemicarbazide; bromobenzohydrazine o,m,p); 2,4-dinitromethylphenylhydrazine; p-carboxphenylhydrazine; nitrobenzenesulfonhydrazine; p-nitrobenzohydrazine; diphenylhydrazine; 2-naphthylhydrazine; p-chlorobenzohydrazine; m-chlorobenzohydrazine; nitroguanylhydrazine; alpha-(alpha,4-nitrophenyl)-alpha-methylhydrazine; xenylsemicarbazide; tolylsemicarbazide (o,m,p); phenylsemicarbazide; 1-naphthylsemicarbazide; 2-naththylsemicarbazide; 3,5-dinitrophenylsemicarbazide; dibromomethone; benzothiazole; benzothiazoline; aminomorpholines; hydrazinobenzoic acid; 5-(1-phenylmethyl)semioxazide 1,3-cyclohexadione; 1,2-bis(p-methoxybenzylamino)ethane or p-hydroxybenzoic acid hydrazide.

* * * * *